United States Patent [19]
Fox et al.

[11] Patent Number: 6,001,565
[45] Date of Patent: Dec. 14, 1999

[54] METHODS, PRIMERS, AND KITS FOR DETECTION AND SPECIATION OF CAMPYLOBACTER

[75] Inventors: Andrew John Fox, East Didsbury; Dennis Mackay Jones, Woodford, both of United Kingdom

[73] Assignee: Public Health Laboratory Service Board, London, United Kingdom

[21] Appl. No.: 08/604,991

[22] PCT Filed: Sep. 9, 1994

[86] PCT No.: PCT/GB94/01967

§ 371 Date: Feb. 29, 1996

§ 102(e) Date: Feb. 29, 1996

[87] PCT Pub. No.: WO95/07362

PCT Pub. Date: Mar. 16, 1995

[30] Foreign Application Priority Data

Sep. 9, 1993 [GB] United Kingdom .................. 9318751

[51] Int. Cl.⁶ .............................. C12Q 1/68; C12P 19/34; C07H 19/00; C07H 21/04
[52] U.S. Cl. ............................ 435/6; 435/91.1; 435/91.2; 536/22.1; 536/24.33
[58] Field of Search ............................ 435/6, 91.1, 91.2; 536/22.1, 24.33

[56] References Cited

FOREIGN PATENT DOCUMENTS 0 350 392  1/1990  European Pat. Off. .

OTHER PUBLICATIONS

New England Biolabs Inc., Beverly, MA pp. 7–31, 1986.
Alm, R.A., et al., "Distribution and Polymorphism of the Flagellin Genes from Isolates of *Campylobacter coli* and *Campylobacter jejuni*," *J. Bacteriol.* 175(10):3051–3057 (May 1993).

Birkenhead, D., et al., "PCR for the Detection and Typing of Campylobacters," *Lett. Appl. Microbiol.* 17(5):235–237 (Nov. 1993).

Bolton, F.J., et al., "Development of a Blood–free Campylobacter Medium: Screening Tests on Basal Media and Supplements, and the Ability of Selected Supplements to Facilitate Aerotolerance," *J. Appl. Bacteriol.* 54(1):115–125(1983).

Giesendorf, B.A.J., et al., "Rapid and Sensitive Detection of Campylobacter spp. in Chicken Products by Using the Polymerase Chain Reaction," *Appl. Env. Microbiol.* 58(12):3804–3808 (Dec. 1992).

Nachamkin, I., et al., "Flagellin Gene Typing of *Campylobacter jejuni* by Restriction Fragment Length Polymorphism Analysis," *J. Clin. Microbiol.* 31(6):1531–1536 (Jun. 1993).

Wegmüller, B., et al., "Direct Polymerase Chain Reaction Detection of *Campylobacter jejuni* and *Campylobacter coli* in Raw Milk and Dairy Products," *Appl. Env. Microbiol.* 59(7):2161–2165 (Jul. 1993).

English–language abstract for European Patent Office Publication No. EP 0 350 392 (Ref. AL1), Derwent WPI Accession No. 90–010125/02.

*Primary Examiner*—Ardin H. Marschel
*Assistant Examiner*—Jezia Riley
*Attorney, Agent, or Firm*—Sterne, Kressler, Goldstein & Fox p.l.l.c.

[57] ABSTRACT

Method for detecing Campylobacter by PCR detection of DNA sequence, highly conserved between species *lari, coli, jejuni* and *upsaliensis*. Speciation between these four is possible as the PCR product is differentially cleaved by restriction endonucleases.

24 Claims, 8 Drawing Sheets

```
tgattaacaaaattatcattttaagaaaaatgtataattaatattctataatcttctc
---------+---------+---------+---------+---------+---------+
actaattgttttaatagtaaaaattcttttttacatattaattataagatattagaagag

D * Q N Y H F * E K M Y N *
* L T K L S F L R K N V * L I F Y N L L    - ttgttatcaaaaatttaaggagaaagtc[atgcatccaggtaatgtag]taaat[acga]
---------+---------+---------+---------+---------+---------+
aacaatagttttaaaattcctctttcagctacgtaggtccattacataatttaatgctg

L L S K I L R R K S M H P G N V L N Y D    -

[tatacagttcc]agatattttatgtttgcgaccatattgtttggcattgttggtatggct
---------+---------+---------+---------+---------+---------+
atatgccaacgttctataaaatacaaacgctggtataacaaaccgtaacaaccataccga

Y T V A R Y F M F A T I L F G I V G M A    -

Alu I              Dra I
ataggaactcttatagcttttcaaatggcatatcctaatttaaattatttaccaggacaa
---------+---------+---------+---------+---------+---------+
tatccttgagaatatcgaaaagtttaccgtataggattaaatttaataaatggtcctgtt

I G T L I A F Q M A Y P N L N Y L P G Q    -
```

CULTURABILITY AND PCR DETECTION OF C. JEJUNI IN A POND WATER MICROCOSM

- → SURFACE VIABLE COUNT
- + DILN DETECTED BY PCR

```
tgattaacaaattatcattttaagaaaaatgtataattaatattctataatcttctc
     ---------+---------+---------+---------+---------+
actaattgtttaatagtaaaattcttttacatattaattataagatattagaagag

D * Q N Y H F * E K M Y N *
* L T K L S F L R K N V * L I F Y N L L ttgttatcaaaaatttaaggagagaagtcgatgcatccaggtaatgtattaaattacgac
     ---------+---------+---------+---------+---------+
aacaatagttttaaatttcctctttcagctactacgtaggtccattacataattaatgctg

L L S K I L R R K S M H P G N V L N Y D tatacgttgcaagatatttatgttcgaccatattgtttgcattgttgtatggct
     ---------+---------+---------+---------+---------+
atatgccaacgttctataaatacaagctggtataacaacgtaacaaccataccga
            Alu I
Y T V A R Y F M F A T I L F G I V G M A Dra I
ataggaactcttatagcttttcaaatggcatatcctaatttaattattaccaggacaa
     ---------+---------+---------+---------+---------+
tatccttgagaatatcgaaaagttaccgtataggattaatttaataaatggtcctgtt

I G T L I A F Q M A Y P N L N Y L P G Q
```

```
                    Dde I
tatgccacttttcaagactt agaccactt catacttcaggtgtgatttttggttttatg
-----------+---------+---------+---------+---------+---------+
atacggtgaaaagttctgaa tctggtgtga agtatgaagtccacactaaaaaccaaatac

Y  A  T  F  S  R  L  R  P  L  H  T  S  G  V  I  F  G  F  M  - ctttcaggattttgggcaac gtattataggt ccgcgtgttcttaaagtgagtatggc
-----------+---------+---------+---------+---------+---------+
gaaagtccctaaacccgttg ccatatatcc aggcgcacaagaatttcactcataccg

L  S  G  I  W  A  T  V  L  Y  R  S  A  C  S  *  S  E  Y  G  - tgagtcaagattttaatggctgttggt       1948
---------+---------+-------
actcagttctaaaattaccgacaacca

SIZE MARKERS ON ENDS

PENNER JEJUNI'S AluI DIGEST

OdeI PENNER JEJUNI'S

Ora I PENNER JEJUNI'S

Alu I     Dde I
UPSALIENSIS PCR's Alu I Dde I

UPSALIENSIS PCR's Dra I CUT

AluI - PENNER / LIOR COLI'S

C. Coli Dde I

Dra I PENNER / LIOR COLI'S

METHODS, PRIMERS, AND KITS FOR DETECTION AND SPECIATION OF CAMPYLOBACTER

CROSS REFERENCE TO RELATED APPLICATION

This application claims priority to International Application PCT/GB94/01967, filed Sep. 9, 1994, which designates the United States of America.

FIELD OF THE INVENTION

This invention relates to the detection and speciation of Campylobacter bacteria, for example in clinical, environmental and food samples. In particular, this invention relates to a method of detecting whether a sample contains Campylobacter and to a method of differentiating between the main Campylobacter species *jejuni, coli, upsaliensis* and *lari*.

BACKGROUND OF THE INVENTION

Campylobacter species are recognised as the most frequent cause of bacterial gastroenteritis in the United Kingdom and many other countries throughout the world. In the U.K. approximately 90% and 10% of case isolates are identified as *Campylobacter jejuni* and *Campylobacter coli* respectively, plus a small number of other species such as *Campylobacter upsaliensis* and *lari*. The majority of the infections are sporadic the source of which remains largely unknown although the importance of several vehicles is now recognised.

There is a known desire to be able to detect and differentiate species of Campylobacter. However, it is also known that present Campylobacter enrichment culture techniques lack sensitivity, making detection difficult. *Campylobacter jejuni* does not multiply in foodstuffs and low numbers may be present together with a high background of indigenous microflora. Also, surface viable counts of Campylobacter can decrease rapidly and cells that are potentially culturable are often lost before samples reach a laboratory for analysis. Another factor making detection problematic is that antibiotics used in culture enrichment media may damage already weakened Campylobacter.

There are currently available assays for detection of a variety of food and water-borne pathogens; *L. pneumophila, V. vulnificus*, enteroinvasive *E. coli*, Shigella; but no satisfactory method of detecting Campylobacter or distinguishing between the four main Campylobacter species is known.

A method of detecting Campylobacter has been published by Giesendorf, B A J, et al in Applied and Environmental Microbiology, December 1992, pages 3804–3808. The method detects the species *jejuni, coli* and *lari*, and produces similar results to conventional methods but in a reduced time. The method suffers from a number of drawbacks. It does not enable detection of the species *upsaliensis*. Further, the method employs polymerase chain reaction (PCR) techniques but nevertheless requires a short enrichment culture before the PCR can be employed. Further still, the primer used for the PCR does not have the precise homology with DNA sequences in the three Campylobacter species that can be detected using the method.

Another method for detecting *Campylobacter jejuni* and *Campylobacter coli* is known from Wegmuller, B E et al, Applied Environmental Microbiology, vol. 59, part 7, 1993 pages 2161–2165. The described method detects only the species *jejuni* and *coli*.

In addition to the above-identified problems with detection and speciation of Campylobacter, recent work on *Campylobacter jejuni* suggests that in certain circumstances it enters a "non-culturable, viable form" when subjected to environmental stresses, such as pH or temperature extremes, increased oxygen tension or nutrient depletion. In this form, Campylobacter infectivity is maintained but-the organisms cannot be cultured. Thus there exists a need for the improvement of methods of detection of non-culturable forms of Campylobacter.

SUMMARY OF THE INVENTION

It is an object of this invention to provide a method of testing for the presence of Campylobacter that enables more efficient detection and eliminates or mitigates the problems with existing techniques. It is a further object to provide a method of distinguishing the Campylobacter species *jejuni, coli, upsaliensis* and *lari*.

DETAILED DESCRIPTION OF THE INVENTION

Accordingly, in a first aspect the present invention provides a method of testing for the presence of Campylobacter, e.g. in a clinical, environmental or food sample, comprising the steps of performing polymerase chain reaction (PCR) using primers adapted to amplify a region selected from (a) a sequence of at least 72 base pairs from SEQ ID NO:1 and (b) a sequence having sufficient homology with (a) such that formation of PCR product is correlated with presence of Campylobacter; and determining if any PCR product is formed.

It is preferred that sequence (b) has at least 75% homology with (a), preferably at least 90% homology and more preferably at least 95% homology. It is also preferred that the primers are at least 12 nucleotides in length, preferably between 19–22 nucleotides in length. In particularly preferred embodiments of the invention the primers consist of at least 12 contiguous nucleotides selected from (1) SEQ ID NO:2 and SEQ ID NO:3, (2) SEQ ID NO:4 and SEQ ID NO:5 and (3) sequences having sufficient homology with (1) or (2) such that formation of PCR product is correlated with presence of Campylobacter.

PCR has become a well known and established tool for DNA analysis. A single gene sequence can be marketed from a large amount of other DNA and amplified to provide a suitable quantity for analysis. The basis of today's PCR was first published in 1971 be Kleppe, E et al, J. Mol. Biol., 1971, 56, 341. Further significant details and improvements on the PCR method have been added by Saiki, R K et al, Science, 1985, 230, 1350 and Mullis, K B, Sci. Am. 1990, 262, 36.

As will be appreciated by a person of skill in the art familiar with the PCR, it is important to operate at a temperature suitable to ensure that the primers used are specific for the sequence desired to be identified and amplified. To this end it is convenient to carry out the PCR reaction using the method of the invention at temperatures of at least 40° C. preferably at least 45° C. and in a particularly preferred embodiment at 48°–52° C.

The 1.9 kilobase fragment identified in SEQ ID NO:1 is an underlying feature of this invention and has been found to be highly conserved between Campylobacter isolates. The method of the invention confers the advantage that PCR product will only be detected when a Campylobacter strain is found in the sample tested. The method also confers the advantage that it will detect non-culturable viable forms of Campylobacter as well as viable cells. Thus the method is effective where other methods have not been able to detect any Campylobacter.

It is preferable to use a primer sequence that will only bind to one specific region of SEQ ID NO:1 and which will not engage in formation of primer dimers and thus contaminate the PCR. Examples of preferred primers for use in the method of the invention are shown in the SEQ ID NOs:2 and 3 and SEQ ID NOs:4 and 5. These primers form further aspects of the invention.

In a second aspect the invention provides a method of distinguishing between Campylobacter species *jejuni, coli, upsaliensis* and *lari* in a DNA containing sample by performing PCR utilizing primers capable of amplifying a selected Campylobacter DNA sequence, said sequence having restriction endonuclease sites specifically associated with different Campylobacter species and then testing for digestion of the PCR product by the specific restriction endonucleases.

Thus, Campylobacter DNA that is differentially cleared by restriction endonucleases is amplified, subject to digestion by the endonucleases and identified as from a particular species.

SEQ ID NO:1 was isolated from *Campylobacter jejuni* and is known to have a particular characteristic pattern of cleavage by restriction endonucleases. *Campylobacter coli, upsaliensis* and *lari* contain sequences corresponding to SEQ ID NO:1 that have altered patterns of cleavage characteristic of each species.

In an embodiment of the second aspect there is provided a method of distinguishing between Campylobacter species *jejuni, coli, upsaliensis* and *lari*, e.g. in a clinical, environmental or food sample containing Campylobacter, comprising the steps of:

performing polymerase chain reaction (PCR) on the sample using primers adapted to amplify a region of DNA SEQ ID NO:1 that includes nucleotides 124–196, or using primers adapted to amplify a DNA region corresponding thereto; and testing the PCR product for digestion by restriction endonucleases Alu I, Dra I and Dde I.

The method of the second aspect is advantageous because it enables accurate speciation between the four clinically most significant species. In particular, when amplifying region 124–196 of SEQ ID NO:1, the PCR product from *Campylobacter jejuni* is cleaved by all three restriction endonucleases, whereas the PCR product from species coli is not cleaved by Dra I, the PCR product from species *upsaliensis* is only cleaved by Dde I and PCR product from *lari* is only cleaved by Alu I. It is a straightforward matter for a person skilled in the art to identify whether the PCR product is cleaved by one or more of the above endonucleases and thus the method enables simple speciation of Campylobacter into *jejuni, coli, upsaliensis* or *lari*.

The embodiments of the first aspect of the invention described above form embodiments of the second aspect of the invention also, provided that primers are selected so as to be adapted to amplify at least nucleotides 124–196 of SEQ ID NO:1, or a Campylobacter sequence corresponding thereto.

In a preferred embodiment of the second aspect the primers consist of at least 12 contiguous nucleotides from SEQ ID NOs: 4 and 5. Where the primers are SEQ ID NOs: 4 and 5 the PCR product is 256 bp and the respective products of cleavage by Alu I, Dra I and Dde I differentiate between *jejuni, coli, upsaliensis* and *lari*.

In a further embodiment of the invention, increased sensitivity and specificity for the detection of the presence of Campylobacter DNA, e.g. in food and liquid samples, is provided by the following additional methodologies:

1. A nested PCR has been developed, and is performed by an additional round of amplification using primer sequences international primer SEQ ID NOs:4 and 5. Two exemplary primer sequences are identified as Cru 0476 (SEQ ID NO:6) and Cru 0474 (SEQ ID NO:7). Following the second round of amplification, an amplicon of approximately 173 pb is obtained in the presence of Campylobacter DNA. This DNA fragment retains the sequences for the restriction endonucleases Alu 1, Dde 1, and Dra 1, thus still enabling the speciation of the contaminating Campylobacter.

2. Additional increased sensitivity and specificity is optionally achieved by southern transfer of the amplified PCR products obtained using oligonucleotide primers having SEQ ID NOs:4 and 5, followed by hybridisation with an internal probe (e.g. SEQ ID NO:8 probe sequence). The probe sequence spans the restriction sites for speciation of the contaminating Campylobacter and therefore restriction digest analysis can be used in conjunction with the probe hybridisation to confer additional specificity. The probe can be labelled, for example with digoxigenin, or radiolabelled.

The extraction procedures for food and environmental samples preferably use an internal standard to enable qualitative estimation of extraction efficiency and the effects of non-specific inhibition. The PCR "MIMIC" (Clontech Laboratories, Palo Alto, Calif.) is a form of competitive PCR in which a non-homologous neutral DNA fragment is engineered containing the same primer templates as the target DNA. The amplimer produced from this construct is a fragment either smaller or larger than the target product. Known amounts of construct are added to the PCR reaction, and compete for the same primers, acting as an internal standard. Where a mimic is used, the mimic sequence is capable of being amplified by the same primers that amplify, under PCR conditions, the Campylobacter sequence. The mimic, if cleaved by restriction endonucleases, does not form fragments that interfere with detection and/or speciation of Campylobacter-the mimic is said to be "neutral".

It is preferred to carry out the PCR steps of the invention also using a mimic. In an example, mimic DNA is added to the sample and PCR is performed according to the invention. The PCR product is analyzed. If mimic DNA has been amplified, this indicates that the PCR reaction has occurred properly. The product can then be tested for products that indicate presence of Campylobacter. If no mimic DNA is amplified then this indicates PCR has not fully been carried out, or has been inhibited in some way.

It is further preferred to carry out PCR using mimic DNA of known and varying quantities. After amplification, the various results are compared and it is observed which of the results has comparable amounts of amplified mimic and (if present) Campylobacter DNA. Thus, an estimate of the quantity of Campylobacter DNA in the original sample is obtained.

EXAMPLES

The methods of the invention are further illustrated by the further embodiments of the invention described in the following Examples:

Example 1

The PCR assay was developed by the following steps:

1> Identification of a highly conserved, species specific clone from a random library of *Campylobacter jejuni* insert fragments, cloned in the vector pBlueScript KS.

2> Chain termination sequencing of the 1.9 kilobase fragment in both directions.

3> Selection of presumptive primer pairs based on regions of equivalent G+C/A+T content, and low identity (prevention of 'primer-dimer').

4> Optimisation of reaction parameters: Mg$^{++}$ concentration, Taq enzyme source, buffer composition, annealing temperature, cycling parameters.

Example 2

ASSESSMENT OF ASSAY SENSITIVITY AND SPECIFICITY

Using a single amplification (35 cycles, annealing temperature 50° C.) we detected approx. 10 CFU/ml of *Campylobacter jejuni*.

At this stringency, the assay was specific for *Campylobacter jejuni*, *Campylobacter coli* and *Campylobacter upsaliensis*. Using a lower annealing temperature (42° C.), *Campylobacter fetus* and *Campylobacter lari* were also amplified.

Example 3

The following procedures were used for PCR amplification of *Campylobacter jejuni* from milk and water samples.

1> cell lysis by boiling or freeze/thaw cycles, centrifuge, PCR supernatant directly.

2> Cell lysis by boiling, nucleic acid purification by phenol\chloroform extraction 3> cell lysis by guanidine isothiocyanate, nucleic acid purification using nuclease binding matrix ("isoquick").

4> Cell concentration using magnetic particles coated with anti-Campylobacter IgG, cell lysis by boiling.

5> concentration and immobilisation of cells on 0.2 μm nitrocellulose filters ('solid-phase' PCR).

6> Cell-concentration using affinity column purification

7> guanidinium isothiocyanate nucleic acid extraction, with purification using silica bead matrix ('boom method')

---
EXTRACTION OF MILK SAMPLES
FOR PCR ANALYSIS
WARM MILK TO 37° C.
↓
CENTRIFUGE @ 3,000xg, 15 MINUTES
↓
CHILL ON ICE SEPARATE MILK AND CREAM
CREAM                           MILK
EMULSIFY IN 10 VOLUMES
WARM PBS
↓                               ↓
CENTRIFUGE @ 9,000xg, 15 MINUTES
DISCARD SUPERNATANT    DISCARD SUPERNATANT
RESUSPEND MILK AND CREAM PELLETS IN
5 VOLUMES OF PBS. POOL EXTRACTS.
↓
BOIL FOR 10 MINUTES
↓
CENTRIFUGE @ 14,000xg, 5 MINUTES
↓
EXTRACT DNA WITH SILICA-BASED PURIFICATION MATRIX
↓
ELUTE NUCLEIC ACIDS WITH 2 × 50 μl PURE WATER
↓
PCR NEAT SAMPLE, AND 10-FOLD SERIAL DILUTIONS
EXTRACTION OF WATER SAMPLES
PRE-FILTRATION THROUGH 30 μm in WHATMAN FILTER
↓
CENTRIFUGE @ 9,000xg, 15 MINUTES
↓
WASH PELLET x2, 1 ML PBS
↓
RESUSPEND IN 1 ML STERILE WATER
↓
BOIL, 10 MINUTES
↓
EXTRACT DNA WITH SILICA-BASED PURIFICATION MATRIX
---

Example 4

We observed the following differentiation of Campylobacter species using PCR primers SEQ ID NO:4 and SEQ ID NO:5 and restriction endonucleases Alu I, Dra I and Dde I.

|  | PCR product digested with: | | |
| --- | --- | --- | --- |
| Species | Alu I | Dra I | Dde I |
| *C. jejuni* | + | + | + |
| *C. coli* | + | − | + |
| *C. upsaliensis* | − | − | + |
| *C. lari* | + | − | − |

We further observed the following fragment sizes for different species.

| | Restriction enzyme digests of PCR amplimers | | |
| --- | --- | --- | --- |
| Species | Alu I | Dde I | Dra I |
| Thermophilic/ enteropathogenic | Fragment sizes (bp) | Fragment sizes (bp) | Fragment sizes (bp) |
| *C. jejuni* | 2  108, 148 | 2  83, 173 | 2  123, 133 |
| *C. jejuni* (hippurate + ve) | 2  108, 148 | 2  83, 173 | 2  123, 133 |
| *C. coli* | 2  108, 148 | 2  83, 173 | 1  256 |
| *C. lari* | 2  108, 148 | 1  256 | 1  256 |
| *C. upsaliensis* | 1  256 | 3  30, 83, 143 | 1  256 |

The results are also illustrated in FIG. 3 where bands were not visible by eye they were detected by use of radiolabels.

Example 5

To test the specificity of Campylobacter detection we used PCR primers on laboratory samples containing a wide range of organisms. The primers were SEQ ID NOs: 4 and 5, PCR product size in brackets:

| | Annealing temperature of primers | | |
| --- | --- | --- | --- |
| Species | 37° C. | 42° C. | 50° C. |
| *C. jejuni* | + (256) | + | + |
| *C. coli* | + | + | + |
| *C. upsaliensis* | + | + | + |
| *C. fetus* | + | ± | − |
| *C. lari* | + | ± | − |
| *C. mucosalis* | ± | − | − |
| *C. sputorum* | ± | − | − |
| *Achromobacter sp.* | − | − | − |
| *Acinetobacter calcoac.* | ± (multiple) | − | − |
| *Acinetobacter sp.* | ± (multiple) | − | − |
| *Aeromonas hydrophila* | − | − | − |
| *Citrobacter* | − | − | − |

-continued

| Species | Annealing temperature of primers | | |
|---|---|---|---|
| | 37° C. | 42° C. | 50° C. |
| freundii | | | |
| Enterobact. aerogenes | − | − | − |
| Enterobact. agglomerans | ± (500) | − | − |
| Enterobacter cloacae | − | − | − |
| Escherichia coli | − | − | − |
| Flavobacterium | − | − | − |
| Klebsiella aerogenes | − | − | − |
| Klebsiella oxytoca | ± (500) | − | − |
| Proteus mirabilis | − | − | − |
| Proteus morganii | − | − | − |
| Providencia stuartii | − | − | − |
| Pseudomonas aeroginosa | − | − | − |
| Pseudomonas maltophilia | − | − | − |
| Pseudomonas pickettii | − | − | − |
| Salmonella enteritidis | − | − | − |
| Salmonella typhimurium | − | − | − |
| Serratia marcescens | − | − | − |
| Serratia liquefaciens | − | − | − |
| Shigella dysenteriae | − | − | − |
| Shigella sonnei | − | − | − |
| Vibrio cholera | − | − | − |
| Vibrio furnassii | ± (1000) | − | − |
| Vibrio parahaemolyticus | ± (180) | ± | − |
| Yersinia enterocolitica | − | − | − |
| Oxford Staphlococcus | ± (300) | ± | − |

Example 6

Using standard culture techniques (published by Bolton F J. et al, J. Appl. Bacteriol., 1983, vol. 54, pages 115–125) we compared the detection of *Campylobacter jejuni* by culture with detection by the method of the invention (using primers SEQ ID NOs: 4 and 5) against time.

The success of culture detection declined over the time of the comparison, no culturable organisms being found remaining in the sample after 26 days—thus at this point detection by culture indicated no Campylobacter present.

By contrast, using the PCR method of the invention we were still able to detect Campylobacter DNA in a sample 42 days old. The results are illustrated in FIG. 1.

Example 7

To confirm the accuracy of the PCR method of the invention we tested many samples that contained known species of Campylobacter. The results, illustrated in FIGS. 4–11, confirm the method is completely accurate for all samples tested, and correctly identified each one by species.

FEATURES OF THE PCR ASSAY FOR *Campylobacter jejuni*

It allows rapid and sensitive detection of *Campylobacter jejuni* from environmental samples, provides a semi-quantitative indication of the bacterial load, and determines whether samples are contaminated with *Campylobacter jejuni, coli, upsaliensis* or *lari*.

The method is of use for examining epidemiology of Campylobacter infection such as a) seasonal peak, b) inverse correlation of surface water viable counts with human disease, c) role of water supply in (re)infection of broiler flocks with *Campylobacter jejuni*, d) contamination of foodstuffs at the point of sale, and e) determine origin of sporadic human infections.

Thus, a novel method incorporating polymerase chain reaction assay has been developed for the detection of Campylobacter in clinical, environmental and food samples, such as milk and water samples. The assay is rapid, highly sensitive, and specific for Campylobacter sp. Simple restriction analysis of the PCR product allows speciation between *Campylobacter jejuni, coli, upsaliensis* and *lari*.

DESCRIPTION OF DRAWINGS

FIG. 1 shows a comparison of culturability of *Campylobacter jejuni* against time with detection of *Campylobacter jejuni* using PCR of the invention;

FIG. 2 shows the sequence (SEQ ID NOs: 12, 14–19) of open reading frame "C" from insert fragment pBSKSCJ19B with primer/nested primer locations, and restriction sites;

Figure 3:
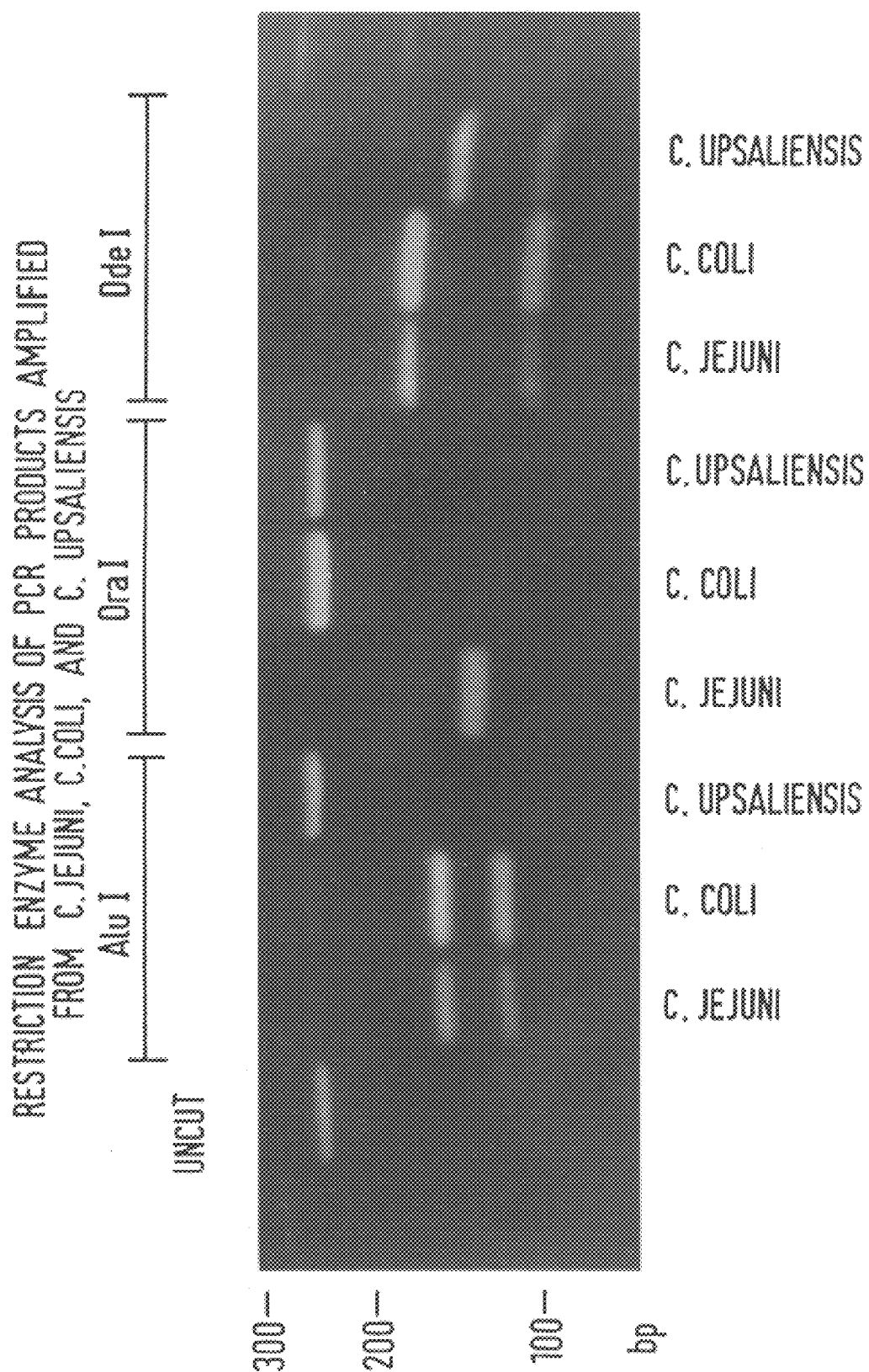
FIG. 3 shows restriction enzyme analysis of PCR products amplified from *C. jejuni, coli* and *upsaliensis*.
Figure 4:
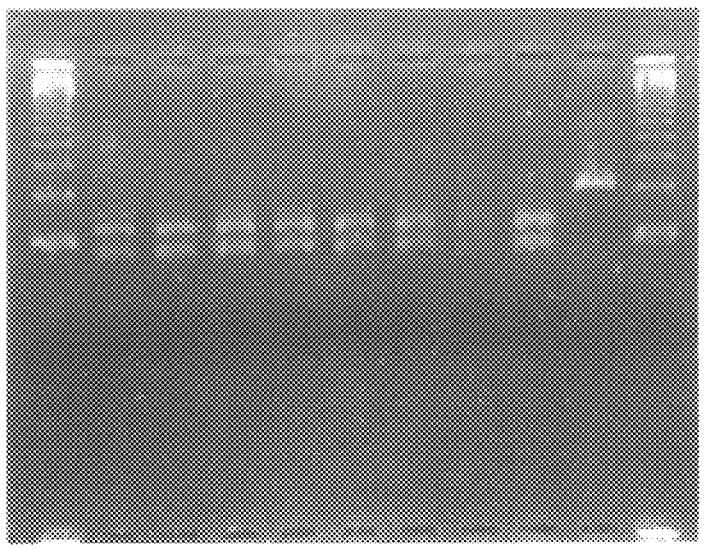
FIGS. 4–11 shows the results of carrying out the PCR method of the invention on samples containing a wide ranges of known isolates. "P"=Penner Serotype Reference strains. "L"=Lior Serotype Reference Strains. Others are laboratory isolates. Standard size markers are on the gel ends.
Figure 5:
Figure 6:
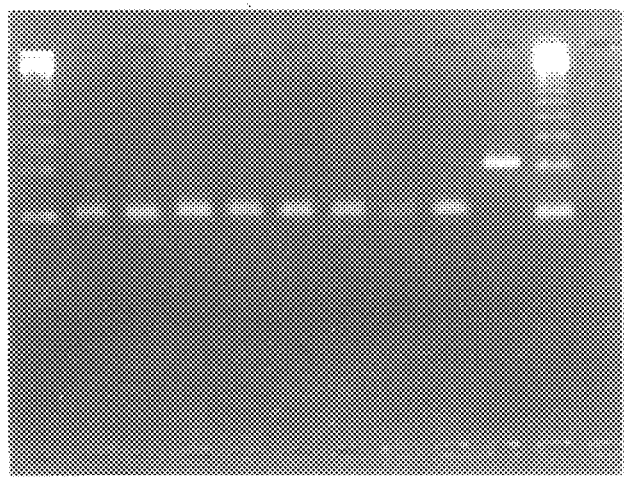
Figure 7:
Figure 8:
Figure 9:
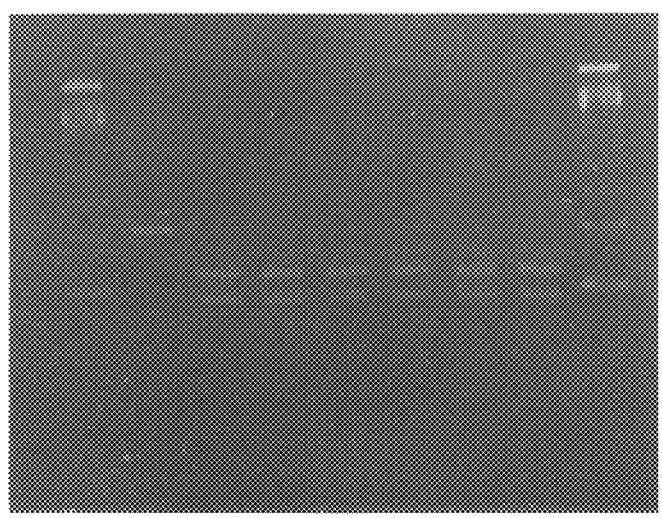
Figure 10:
Figure 11:
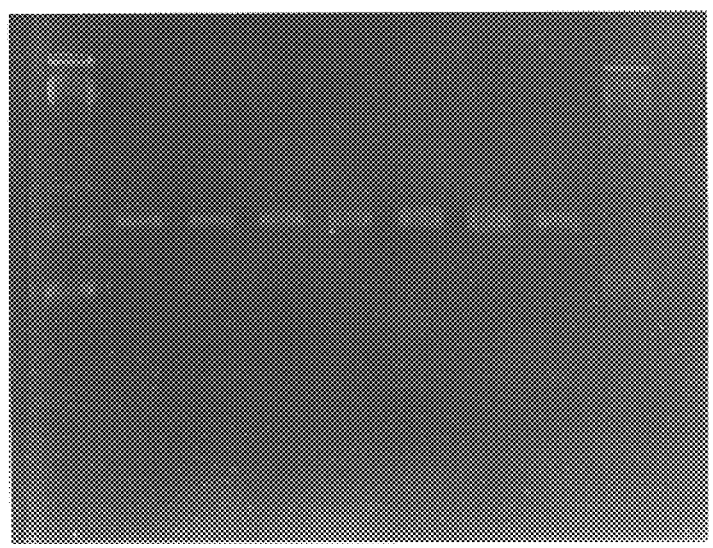

| FIG. 4 | C. Jejuni. | Alu I digest. |
| FIG. 5 | C. Jejuni. | Dde I digest. |
| FIG. 6 | C. Jejuni. | Dra I digest. |
| FIG. 7 | C. upsaliensis. | Alu I and Dde I digest. |
| FIG. 8 | C. upsaliensis. | Dra I digest. |
| FIG. 9 | C. Coli. | Alu I digest |
| FIG. 10 | C. Coli. | Dde I digest |
| FIG. 11. | C. Coli. | Dra I digest |

Sequence ID No. 1

```
  1 accaacagcc attaaaaatc ttgactcagc catactcact ttaagaacac
    tggttgtcgg taatttttag aactgagtcg gtatgagtga aattcttgtg 51 gcggacctat ataataccgt tgcccaaatc cctgaaagca taaaaccaaa
    cgcctggata tattatggca acgggtttag ggactttcgt attttggttt 101 attcacacct gaagtatgaa gtggtctaag tcttgaaaaa gtggcatatt
```

-continued

```
     ttagtctgga cttcatactt caccagattc agaactttt caccgtataa 151 gtcctggtaa ataatttaaa ttaggatatg ccatttgaaa agctataaga
     caggaccatt tattaaattt aatcctatac ggtaaacttt tcgatattct 201 gttcctatag ccataccaac aatgccaaac aatatggtcg caaacataaa
     caaggatatc ggtatggttg ttacggtttg ttataccagc gtttgtattt 251 atatcttgca accgtatagt cgtaatttaa tacattacct ggatgcatcg
     tatagaacgt tggcatatca gcattaaatt atgtaatgga cctacgtagc 301 actttctcct taaaatttt gataacaaga gaagattata gaatattaat
     tgaaagagga attttaaaaa ctattgttct cttcaatat cttataatta 351 tatacatttt ttcttaaaaa tgat/aattt gttaatcatt tgttatgttt
     atatgtaaaa aagaattttt acta t-
     taaaa caattagtaa acaatacaaa 401 tatatttaa ggctaaatca gtcttattta ttgatattta tcttataacc
     atataaaatt ccgatttagt cagaataaat aactataaat agaatattgg 451 taaacttgtc acattttta taaaatcttc acccactta tctcttactc
     atttgaacag tgtaaaaaat atttta-
     gaag tgggttgaaat agagaatgag 501 tttttataaa agttcta{aca gcagtatcgc tcacatgt}c acctatccaa
     aaaaatattt tcaagat tgt cgtcat-
     agcg agtgtaca g tggataggtt 551 acatttttct taatatcttc atgcaaaacc aaagctccag gttgctttaa
     tgtaaaaaga attatagaag tacgttttgg tttcgaggtc caacgaaatt 601 aagcaaagaa ataaaagcca attctttttt agttaaaaca atttctccac
     ttcgtttctt tattttcggt taagaaaaaa tcaattttgt taaagaggtg 651 cactgtaaat taaagttcgt ttattttgt taaattgata ttcttcagaa
     gtgacattta atttcaagca aataaaaaca atttaactat aagaagtctt 701 attttttacaa gcatatttgc ttcaatttt tcacctatca gataatctaa
     taaaaatgtt cgtataaacg aagttaaaaa agtggatagt ctattagatt 751 aactttaaac aactcttcta tatcaacagg tttaatcaaa tatttatcta
     ttgaaatttg ttgagaagat atagttgtcc aaattagttt ataaatagat 801 taccaatatc aatagaacgc aaaagtctct ctt tctctga atacgcacta
     atggttatag ttatcttgcg ttttcagaga gaa{agagact tatgcgtgat 851 aga acaacaa ttgggacatc atctgaaatt tctttaatct ctcttgccat
     tct tgttgaa aaccctgtag tagactttaa agaaattaga gagaacggta 901 atccagtcca tccataatag gcatagcaat atctgtgata actaaatctg
     taggtcaggt aggtattatc cgtatcgtta tagacactat tgatttagac 951 gcttaaattt tttaaatttt ttaagcccct catctccatt ttgagctccg
     cgaatttaaa aaatttaaaa aattcggggt gtagaggtaa aactcgaggc 1001 attactttac taaagcgttc gcttaatata ttaatcattg attctctagc
     taatgaaatg atttcgcaag cgaattatat aattagtaac taagagatcg 1051 cttaacctca tcttcaacta ctaatattat taattctta cattcttgtg
     gaattggagt agaagttgat gattataata attaagaaat gtaagaacac 1101 acat/ttctac tctaccctct cttttagttt taaaaatatc tcaaaacaag
     tgta aagatg agatgggaga gaaatcaaa attttatag agttttgttc 1151 ccccgtcttt tccatttta acttttattt ttccttggaa actttcgata
     ggggcagaaa aggtaaaaat tgaaaataaa aaggaacctt tgaaagctat 1201 atttgtctac ttatataaag tcctactcct ataccttgac taggatgttt
     taaacagatg aatatatttc aggatgagga tatggaactg atcctacaaa 1251 tgttgtaaaa taaggttgaa aaatttttatc taaattttct ttatcaatcc
     acaacatttt attccaactt tttaaaatag atttaaaaga aatagttagg 1301 caccagcatt atcttttatt gtaattttca gataattttt tccaaatttt
     gtggtcgtaa tagaaaataa cattaaaagt ctattaaaaa aggtttaaaa 1351 gaaaaattta ttgttatgat tttccttttt ttgttttaa atgcttctat
     cttttaat aacaatacta aaggaaaaa aacaaaaatt tacgaagata 1401 tgaatttaaa atcaaattaa gaaaaactct tattaaacca ttctcatatg
```

-continued

```
     acttaaattt tagtttaatt cttttgaga ataatttggt aagagtatac
1451 ccaaaacttc ataatcactt ttcgaaacaa tattaatatt tacatgattt
     ggttttgaag tattagtgaa aagctttgtt ataattataa atgtactaaa
1501 ttttctatag tttcaaaagc aatttccaag gctttatta aagtctcttt
     aaaagatatc aaagttttcg ttaaaggttc cgaaataaat ttcagagaaa
1551 tataaataca cactgctcta ctcctttgtt aaacaaagtt ctaaacacat
1601 caattgtttc tgacatattt ttaatcatat cttttgattg tgagtaaatt
     gttaacaaag actgtataaa aattagtata gaaaactaac actcatttaa
1651 tcagcaaatc cttttttcatc tttaagattt tgcttcattt gaaacatggc
     agacgtttag gaaaaagtag aaattctaaa acgaagtaaa ctttgtaccg
1701 aataccgagc tcatttaacg gttgtctcca ttgatgtgct atatcactaa
     ttatggctcg agtaaattgc caacagaggt aactacacga tatagtgatt
1751 tcatttgttc taatgaagat ttcaaaatct cttcatatgc tattttaata
     agtaaacaag attacttcta aagttttaga gaagtatacg ataaaattat
1801 tcttttttcat ttttttccaa ggcaatttgc attttttttct caaatttttt
     agaaaaagta aaaaaggtt ccgttaaacg taaaaaaaga gtttaaaaaa
1851 acctaactgt ataaattctt ggtggtgatt tttaactgta ttttcaagat
     tggattgaca tatttaagaa caaccactaa aaattgacat aaaagaacta
1901 taatacttaa ttctcttaat ttagcgtgat ttagagcaag ctcttcat
     attatgaatt aagagaatta aatcgcacta aatctcgttc gagaagta
```

Sequence ID No. 2
5' TCTTAGTGCG TATTCAGAGA 3'

Sequence ID No. 3
5' ACAGCAGTAT CGCTCACATG T 3'

Sequence ID No. 4
5' AGAACACGCG GACCTATATA 3'
(also referred to as B04263)

Sequence ID No. 5
5' CGATGCATCC AGGTAATGTA T 3'
(also referred to as B04264)

-continued

Primer Sequences

Internal

Cru 0476 (SEQ ID NO: 6)
5' a t c a c a c c t g a a g t a t g a 3' 18 mer

Cru 0474 (SEQ ID NO: 7)
5' t a c g a c t a t a c g g t t g c a 3' 18 mer

Amplimer size: 173 base pairs

---

SEQ ID NO: 8
Probe sequence (173 bp amplimer from nested primers)

```
tacgactatacggttgcaagatattttatgtttgcg
-----+---------+---------+---------+
atgctgatatgccaacgttctataaaatacaaacgc
 Y   D   Y   T   V   A   R   Y   F   M   F   A accatattgtttggcattgttggtatggct
     ---------+---------+---------+1740
     tggtataacaaaccgtaacaaccataccga
      T   I   L   F   G   I   V   G   M   A   -

Alu I
     ataggaactcttatagcttttcaaatggca
1741 ---------+---------+---------+
     tatccttgagaatatcgaaaagtttaccgt
      I   G   T   L   I   A   F   Q   M   A   -

Dra I
     tatcctaatttaaattatttaccaggacaa
     ---------+---------+---------+1800
     ataggattaaatttaataaatggtcctgtt
      Y   P   N   L   N   Y   L   P   G   Q   -
```

```
         tatgccacttttcaagacttagaccacttcatacttcaggtgtgat
   1801 ---------+---------+---------+---------+-------
         atacggtgaaaaagttctgaatctggtgaagtatgaagtccacacta
          Y  A  T  F  S  R  L  R  P  L  H  T  S  G  V  I
```

PCR MIMIC primers and sequence

<u>Primer 1</u>   Cru 0477   (SEQ ID NO: 9)
5'        agaacacgcggacctatatacgcaagtgaaatctcctccg   3'    40 mer <u>Primer 2</u>   Cru 0660   (SEQ ID NO: 10)
5'        cgatgcatccaggtaatgtattctgtcaatgcagtttgtag   3'    41mer <u>MIMIC SEQUENCE</u>        (SEQ ID NO: 11)

5'        agaacacgcg gacctatata cgcaagtgaa atctcctccg
          tcttggagaa gggagagcgt ttgccccagc taccattgat
          gtgtacatga tcatggtcaa atgctggatg attgatgcag
          acagccgtcc caagtttcgt gagctgattg cagagttctc
          caaaatggct cgtgaccctc cccgctatct tgttatacag
          ggagatgaaa ggatgcactt gcctagccct acagattcca
          agttttatcg caccctgatg gaggaggagg acatggaaga
          cattgtggat gcagatgagt atcttgtccc acaccagggc
          tttttcaaca tgccctctac atctcggact ctacaaactg
          gttcattgag cgctactagc aacaattctg ctacaaactg
          cattgacaga        3'

---

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 1947 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Campylobacter coli (xi) SEQUENCE DESCRIPTION: SEQ ID NO: 1:

```
ACCAACAGCC ATTAAAAATC TTGACTCAGC CATACTCACT TTAAGAACAC GCGGACCTAT     60

ATAATACCGT TGCCCAAATC CCTGAAAGCA TAAAACCAAA AATCACACCT GAAGTATGAA    120

GTGGTCTAAG TCTTGAAAAA GTGGCATATT GTCCTGGTAA ATAATTTAAA TTAGGATATG    180

CCATTTGAAA AGCTATAAGA GTTCCTATAG CCATACCAAC AATGCCAAAC AATATGGTCG    240

CAAACATAAA ATATCTTGCA ACCGTATAGT CGTAATTTAA TACATTACCT GGATGCATCG    300

ACTTTCTCCT TAAAATTTTT GATAACAAGA GAAGATTATA GAATATTAAT TATACATTTT    360

TTCTTAAAAA TGATAATTTT GTTAATCATT TGTTATGTTT TATATTTTAA GGCTAAATCA    420

GTCTTATTTA TTGATATTTA TCTTATAACC TAAACTTGTC ACATTTTTTA TAAAATCTTC    480

ACCCACTTTA TCTCTTACTC TTTTTATAAA AGTTCTAACA GCAGTATCGC TCACATGTCA    540

CCTATCCAAA CATTTTTCTT AATATCTTCA TGCAAAACCA AAGCTCCAGG TTGCTTTAAA    600

AGCAAAGAAA TAAAAGCCAA TTCTTTTTTA GTTAAAACAA TTTCTCCACC ACTGTAAATT    660

AAAGTTCGTT TATTTTTGTT AAATTGATAT TCTTCAGAAA TTTTTACAAG CATATTTGCT    720

TCAATTTTTT CACCTATCAG ATAATCTAAA ACTTTAAACA ACTCTTCTAT ATCAACAGGT    780
```

-continued

```
TTAATCAAAT ATTTATCTAT ACCAATATCA ATAGAACGCA AAAGTCTCTC TTTCTCTGAA        840

TACGCACTAA GAACAACAAT TGGGACATCA TCTGAAATTT CTTTAATCTC TCTTGCCATA        900

TCCAGTCCAT CCATAATAGG CATAGCAATA TCTGTGATAA CTAAATCTGG CTTAAATTTT        960

TTAAATTTTT TAAGCCCCTC ATCTCCATTT TGAGCTCCGA TTACTTTACT AAAGCGTTCG       1020

CTTAATATAT TAATCATTGA TTCTCTAGCC TTAACCTCAT CTTCAACTAC TAATATTATT       1080

AATTCTTTAC ATTCTTGTGA CATTTCTACT CTACCCTCTC TTTTAGTTTT AAAAATATCT       1140

CAAAACAAGC CCCGTCTTTT CCATTTTTAA CTTTTATTTT TCCTTGGAAA CTTTCGATAA       1200

TTTGTCTACT TATATAAAGT CCTACTCCTA TACCTTGACT AGGATGTTTT GTTGTAAAAT       1260

AAGGTTGAAA AATTTTATCT AAATTTTCTT TATCAATCCC ACCAGCATTA TCTTTTATTG       1320

TAATTTTCAG ATAATTTTTT CCAAATTTTG AAAAATTTAT TGTTATGATT TTCCTTTTTT       1380

TGTTTTTAAA TGCTTCTATT GAATTTAAAA TCAAATTAAG AAAAACTCTT ATTAAACCAT       1440

TCTCATATGC CAAAACTTCA TAATCACTTT TCGAAACAAT ATTAATATTT ACATGATTTT       1500

TTTCTATAGT TTCAAAAGCA ATTTCCAAGG CTTTATTTAA AGTCTCTTTT ATAAATACAC       1560

ACTGCTCTAC TCCTTTGTTA AACAAGTTC TAAACACATC AATTGTTTCT GACATATTTT       1620

TAATCATATC TTTTGATTGT GAGTAAATTT CAGCAAATCC TTTTTCATCT TTAAGATTTT       1680

GCTTCATTTG AAACATGGCA ATACCGAGCT CATTTAACGG TTGTCTCCAT TGATGTGCTA       1740

TATCACTAAT CATTTGTTCT AATGAAGATT TCAAAATCTC TTCATATGCT ATTTTAATAT       1800

CTTTTTCATT TTTTTCCAAG GCAATTTGCA TTTTTTTCTC AAATTTTTTA CCTAACTGTA       1860

TAAATTCTTG TTGGTGATTT TTAACTGTAT TTTCAAGATT AATACTTAAT TCTCTTAATT       1920

TAGCGTGATT TAGAGCAAGC TCTTCAT                                          1947

(2) INFORMATION FOR SEQ ID NO: 2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 2:

TCTTAGTGCG TATTCAGAGA                                                    20

(2) INFORMATION FOR SEQ ID NO: 3:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 3:

ACAGCAGTAT CGCTCACATG T                                                  21

(2) INFORMATION FOR SEQ ID NO: 4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

(ii) MOLECULE TYPE: DNA (genomic)

(xi) SEQUENCE DESCRIPTION: SEQ ID NO: 4:

AGAACACGCG GACCTATATA                                           20

(2) INFORMATION FOR SEQ ID NO: 5:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 5:

CGATGCATCC AGGTAATGTA T                                         21

(2) INFORMATION FOR SEQ ID NO: 6:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 6:

ATCACACCTG AAGTATGA                                             18

(2) INFORMATION FOR SEQ ID NO: 7:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 7:

TACGACTATA CGGTTGCA                                             18

(2) INFORMATION FOR SEQ ID NO: 8:

(i) SEQUENCE CHARACTERISTICS:
         (A) LENGTH: 173 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 8:

TACGACTATA CGGTTGCAAG ATATTTTATG TTTGCGACCA TATTGTTTGG CATTGTTGGT    60

ATGGCTATAG GAACTCTTAT AGCTTTTCAA ATGGCATATC CTAATTTAAA TTATTTACCA   120

GGACAATATG CCACTTTTTC AAGACTTAGA CCACTTCATA CTTCAGGTGT GAT          173

(2) INFORMATION FOR SEQ ID NO: 9:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 9:

```
AGAACACGCG GACCTATATA CGCAAGTGAA ATCTCCTCCG                    40
```

(2) INFORMATION FOR SEQ ID NO: 10:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
CGATGCATCC AGGTAATGTA TTCTGTCAAT GCAGTTTGTA G                  41
```

(2) INFORMATION FOR SEQ ID NO: 11:

(i) SEQUENCE CHARACTERISTICS:
        (A) LENGTH: 410 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 11:

```
AGAACACGCG GACCTATATA CGCAAGTGAA ATCTCCTCCG TCTTGGAGAA GGGAGAGCGT    60

TTGCCCCAGC TACCATTGAT GTGTACATGA TCATGGTCAA ATGCTGGATG ATTGATGCAG   120

ACAGCCGTCC CAAGTTTCGT GAGCTGATTG CAGAGTTCTC CAAAATGGCT CGTGACCCTC   180

CCCGCTATCT TGTTATACAG GGAGATGAAA GGATGCACTT GCCTAGCCCT ACAGATTCCA   240

AGTTTTATCG CACCCTGATG GAGGAGGAGG ACATGGAAGA CATTGTGGAT GCAGATGAGT   300

ATCTTGTCCC ACACCAGGGC TTTTTCAACA TGCCCTCTAC ATCTCGGACT CCTCTTCTGA   360

GTTCATTGAG CGCTACTAGC AACAATTCTG CTACAAACTG CATTGACAGA             410
```

(2) INFORMATION FOR SEQ ID NO: 12:

(i) SEQUENCE CHARACTERISTICS:
        (A) LENGTH: 388 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 12:

```
TGATTAACAA AATTATCATT TTTAAGAAAA AATGTATAAT TAATATTCTA TAATCTTCTC    60

TTGTTATCAA AAATTTTAAG GAGAAAGTCG ATGCATCCAG GTAATGTATT AAATTACGAC   120

TATACGGTTG CAAGATATTT TATGTTTGCG ACCATATTGT TTGGCATTGT TGGTATGGCT   180

ATAGGAACTC TTATAGCTTT TCAAATGGCA TATCCTAATT TAAATTATTT ACCAGGACAA   240

TATGCCACTT TTTCAAGACT TAGACCACTT CATACTTCAG GTGTGATTTT TGGTTTTATG   300

CTTTCAGGGA TTTGGGCAAC GGTATTATAT AGGTCCGCGT GTTCTTAAAG TGAGTATGGC   360

TGAGTCAAGA TTTTTAATGG CTGTTGGT                                   388
```

(2) INFORMATION FOR SEQ ID NO: 13:

(i) SEQUENCE CHARACTERISTICS:
        (A) LENGTH: 58 amino acids
        (B) TYPE: amino acid (D) TOPOLOGY: linear (ii) MOLECULE TYPE: protein (xi) SEQUENCE DESCRIPTION: SEQ ID NO: 13:

Tyr Asp Tyr Thr Val Ala Arg Tyr Phe Met Phe Ala Thr Ile Leu Phe
1               5                   10                  15

Gly Ile Val Gly Met Ala Ile Gly Thr Leu Ile Ala Phe Gln Met Ala
            20                  25                  30

Tyr Pro Asn Leu Asn Tyr Leu Pro Gly Gln Tyr Ala Thr Phe Ser Arg
        35                  40                  45

Leu Arg Pro Leu His Thr Ser Gly Val Ile
50                  55

(2) INFORMATION FOR SEQ ID NO: 14:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 14:

Gln Asn Tyr His Phe
1               5

(2) INFORMATION FOR SEQ ID NO: 15:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 15:

Glu Lys Met Tyr Asn
1               5

(2) INFORMATION FOR SEQ ID NO: 16:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (xi) SEQUENCE DESCRIPTION: SEQ ID NO: 16:

Leu Thr Lys Leu Ser Phe Leu Arg Lys Asn Val
1               5                   10

(2) INFORMATION FOR SEQ ID NO: 17:

(i) SEQUENCE CHARACTERISTICS:
            (A) LENGTH: 102 amino acids
            (B) TYPE: amino acid
            (D) TOPOLOGY: linear (ii) MOLECULE TYPE: peptide (xi) SEQUENCE DESCRIPTION: SEQ ID NO: 17:

Leu Ile Phe Tyr Asn Leu Leu Leu Ser Lys Ile Leu Arg Arg Lys
1               5                   10                  15

Ser Met His Pro Gly Asn Val Leu Asn Tyr Asp Tyr Thr Val Ala Arg
            20                  25                  30

```
Tyr Phe Met Phe Ala Thr Ile Leu Phe Gly Ile Val Gly Met Ala Ile
            35                  40                  45

Gly Thr Leu Ile Ala Phe Gln Met Ala Tyr Pro Asn Leu Asn Tyr Leu
    50                  55                  60

Pro Gly Gln Tyr Ala Thr Phe Ser Arg Leu Arg Pro Leu His Thr Ser
65                  70                  75                  80

Gly Val Ile Phe Gly Phe Met Leu Ser Gly Ile Trp Ala Thr Val Leu
                85                  90                  95

Tyr Arg Ser Ala Cys Ser
                100

(2) INFORMATION FOR SEQ ID NO: 18:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 18:

Ser Glu Tyr Gly
1

(2) INFORMATION FOR SEQ ID NO: 19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 19:

Val Lys Ile Phe Asn Gly Cys Trp
1               5
```

We claim:

1. A method of testing for the presence of Campylobacter in a clinical, environmental or food sample comprising the steps of:

performing polymerase chain reaction (PCR) using primers adapted to amplify a region of at least 72 base pairs from SEQ ID NO:1, wherein the formation of PCR product is correlated with presence of Campylobacter; and determining if any PCR product is formed.

2. A method according to claim 1, wherein the primers comprise at least 12 nucleotides.

3. A method according to claim 2, wherein the primers comprise at least 12 nucleotides.

4. A method according to claim 2, wherein the primers consist of at least 12 nucleotides selected from the group consisting of:

(a) SEQ ID NO:2 and SEQ ID NO:3, and (b) SEQ ID NO:4 and SEQ ID NO:5.

5. A method according to claim 1, wherein the temperature of the PCR is sufficiently high to prevent the primers annealing with non-Campylobacter DNA.

6. A method according to claim 5, wherein the PCR temperature is at least 40° C.

7. A method according to claim 6, wherein the PCR temperature is at least 45° C.

8. A method according to claim 7, wherein the PCR temperature is 48°–52° C.

9. A method of distinguishing between Campylobacter species *jejuni, coli, upsaliensis* and *lari* in a DNA containing sample by performing PCR utilizing primers capable of amplifying a selected Campylobacter DNA sequence comprising at least 72 base pairs, from SEQ ID NO:1, said sequence having restriction endonuclease sites specifically associated with the different Campylobacter species, obtaining PCR product and then testing for digestion of the PCR product by each of the restriction endonucleases Alu I, Dra I and Dde I, wherein the selected Campylobacter sequence is differentially cleaved by said restriction endonucleases.

10. A method of distinguishing between Campylobacter species *jejuni, coli* and *upsaliensis* comprising the steps of:

performing polymerase chain reaction (PCR) using primers adapted to amplify a region of SEQ ID NO:1 that comprises nucleotides 124–196, or using primers adapted to amplify a region of Campylobacter DNA corresponding thereto; and testing the PCR product for digestion by restriction endonucleases Alu I, Dra I and Dde I.

11. A method according to claim 9, wherein *Campylobacter jejuni* DNA is characterised by cleavage by all three endonucleases, *coli* DNA is characterised by lack of cleavage by Dra I endonuclease, *upsaliensis* DNA is characterised by lack of cleavage by Alu I and Dra I endonucleases and *lari* DNA is characterised by cleavage by Alu I endonuclease only.

12. A method according to claim 9, wherein the primers are selected from the group consisting of SEQ ID NOs: 2, 3, 4 and 5.

13. Use of restriction endonucleases Alu I, Dra I and Dde I in differentiating between Campylobacter species *jejuni, coli, upsaliensis* and *lari* by testing for the digestion of a nucleotide sequence comprising SEQ ID NO:1, wherein said nucleotide sequence is differentially cleaved by said restriction endonucleases.

14. A PCR primer consisting of the sequence of SEQ ID NO:2.

15. A PCR primer consisting of the sequence of SEQ ID NO:3.

16. A PCR primer consisting of the sequence of SEQ ID NO:4.

17. A PCR primer consisting of the sequence of SEQ ID NO:5.

18. A PCR primer consisting of a sequence selected from the group consisting of SEQ ID NOs:6, 7, 9 and 10.

19. A kit for detesting Campylobacter comprising a PCR primer according to any one of claims 14–18.

20. A kit for determining Campylobacter species comprising (a) restrictions endonucleases Alu I, Dra I and Dde I, and (b) a PCR primer consisting of a sequence selected from the group consisting of SEQ ID NOs: 2–7, 9, and 10.

21. A method according to claim 10, wherein *Campylobacter jejuni* DNA is characterised by cleavage by all three endonucleases, *coli* DNA is characterised by lack of cleavage by Dra I endonuclease, *upsaliensis* DNA is characterised by lack of cleavage by Alu I and Dra I endonucleases and *lari* DNA is characterised by cleavage by Alu I endonuclease only.

22. A method of distinguishing between Campylobacter species, *jejuni, coli, upsaliensis* and *lari* in a DNA-containing sample by performing PCR utilizing primers capable of amplifying a selected Campylobacter DNA sequence, said sequence comprising restriction endonuclease sites associated specifically with said Campylobacter species, obtaining a PCR product and then testing for digestion of the PCR product by each of the restriction endonucleases AluI, DraI and DdeI, wherein said selected Campylobacter DNA sequence is differentially cleaved by said restriction endonucleases.

23. A method according to claim 22, wherein *Campylobacter jejuni* DNA is characterised by cleavage by all three endonucleases, *coli* DNA is characterised by lack of cleavage by DraI endonuclease, *upsaliensis* DNA is characterised by cleavage by DdeI endonuclease only, and *lari* DNA is characterised by cleavage by AluI endonuclease only.

24. A method of testing for the presence of Campylobacter in a clinical, environmental or food sample, comprising performing PCR using primers adapted to amplify a sequence that is essentially homologous to SEQ ID NO:1 or a fragment thereof comprising at least 72 nucleotides, wherein the formation of PCR product is correlated with presence of Campylobacter, and determining if any PCR product is formed.

\* \* \* \* \*